United States Patent
Elliott et al.

(10) Patent No.: US 10,016,632 B2
(45) Date of Patent: Jul. 10, 2018

(54) OXYGEN FLOW INDICATOR USING FLOW-POWERED ILLUMINATION

(71) Applicant: B/E Aerospace, Inc., Wellington, FL (US)

(72) Inventors: Andrew Elliott, Shawnee, KS (US); Mrinal Nagrecha, Wichita, KS (US)

(73) Assignee: B/E Aerospace, Inc., Winston-Salem, NC (US)

( * ) Notice: Subject to any disclaimer, the term of this patent is extended or adjusted under 35 U.S.C. 154(b) by 526 days.

(21) Appl. No.: 14/573,966

(22) Filed: Dec. 17, 2014

(65) Prior Publication Data
US 2015/0196784 A1    Jul. 16, 2015

Related U.S. Application Data

(60) Provisional application No. 61/918,974, filed on Dec. 20, 2013.

(51) Int. Cl.
*A62B 9/00* (2006.01)
*A62B 7/12* (2006.01)
(Continued)

(52) U.S. Cl.
CPC ............... *A62B 9/006* (2013.01); *A62B 7/12* (2013.01); *A62B 7/14* (2013.01); *A62B 18/02* (2013.01);
(Continued)

(58) Field of Classification Search
CPC .......... A61M 16/0051; A61M 16/0411; A61M 16/08; A61M 16/0841–16/0858;
(Continued)

(56) References Cited

U.S. PATENT DOCUMENTS 5,005,572 A * 4/1991 Raemer ............. A61M 16/0488
128/205.23
5,857,460 A * 1/1999 Popitz ................. A61M 16/06
128/204.22
(Continued)

FOREIGN PATENT DOCUMENTS

EP     1 099 910 A2   5/2001
FR     2654057 A1     5/1991
(Continued)

OTHER PUBLICATIONS

International Search Report, dated Apr. 30, 2015, 5 pages, from PCT/US14/071722, published as WO 2015/095823 on Jun. 25, 2015.
(Continued)

*Primary Examiner* — Valerie L Woodward
(74) *Attorney, Agent, or Firm* — Donna P. Suchy

(57) ABSTRACT

A flow indicator of a breathing apparatus that indicates a flow of a breathing-gas includes a structure within a conduit for delivering the breathable gas, where the structure undergoes a change as a result of a presence of the breathable gas or a movement of the breathable gas past the structure. The flow indicator also includes a gas flow display that is actuated by the change in the structure to visually indicate a presence or flow of the breathable gas, where the display is powered by the change in the structure without any outside power supply.

14 Claims, 3 Drawing Sheets

(51) Int. Cl.
  *A62B 7/14* (2006.01)
  *A62B 18/02* (2006.01)
  *G01P 13/00* (2006.01)
  *G01F 1/28* (2006.01)
  *A61M 16/06* (2006.01)

(52) U.S. Cl.
  CPC .......... *G01P 13/0006* (2013.01); *A61M 16/06* (2013.01); *A61M 2202/0208* (2013.01); *G01F 1/28* (2013.01)

(58) Field of Classification Search
  CPC ...... A61M 16/0875; A61M 2016/0015; A61M 2016/0027–2016/0042; A61M 2016/0413; A62B 9/006; A62B 18/088
  See application file for complete search history.

(56) References Cited

U.S. PATENT DOCUMENTS

| | | | |
|---|---|---|---|
| 6,331,438 B1* | 12/2001 | Aylott | G01N 21/66 422/82.07 |
| 6,910,481 B2* | 6/2005 | Kimmel | A61M 16/0051 128/202.22 |
| 7,298,280 B2 | 11/2007 | Voege et al. | |
| 7,718,130 B1* | 5/2010 | Shinar | G01N 21/6454 250/458.1 |
| 7,730,847 B1 | 6/2010 | Redd et al. | |
| 7,925,143 B1 | 4/2011 | Lapwood | |
| 2006/0191353 A1* | 8/2006 | Sood | B82Y 10/00 73/861.02 |
| 2012/0325215 A1* | 12/2012 | Levenick | A61M 16/08 128/205.23 |

FOREIGN PATENT DOCUMENTS

| WO | WO-2008/008324 A2 | 1/2008 |
|---|---|---|
| WO | 2008109929 A1 | 9/2008 |

OTHER PUBLICATIONS

Office Action dated Jul. 27, 2016 in European Patent Application No. 14825237.2.
Written Opinion dated Apr. 30, 2015 in PCT/US2014/071722 filed Dec. 19, 2014 (submitting English translation only).
Office Action of European Patent Office Application No. 14736564.7, dated Jun. 8, 2017, 5 pages.
Second Office Action (with translation) of Chinese Patent Application No. 201480034838.0, dated Jun. 16, 2017, 5 pages.
Office Action on Canadian Patent Application No. 2,915,813 dated Apr. 19, 2018. 3 pages.
Office Action on Canadian Patent Application No. 2,933,615 dated Apr. 19, 2018. 3 pages.

* cited by examiner

OXYGEN FLOW INDICATOR USING FLOW-POWERED ILLUMINATION

CROSS-REFERENCES TO RELATED APPLICATIONS

This application claims priority from U.S. Application No. 61/918,974, filed Dec. 20, 2013, the content of which is incorporated by reference in its entirety.

BACKGROUND

The present invention relates generally to oxygen masks used by airline passengers, medical patients, emergency rescue personnel, and the like, and more particularly to an oxygen mask and oxygen supply system that uses the flow of the gas through the delivery line to power an indicator indicating the presence of the flow itself, eliminating the need for a separate power system for the indicator.

Flow indication technology is extremely vital in, for example, the life support systems industry, utilized in aircraft/helicopters, as well as in hospitals. Passengers and patient's oxygen intake is extremely vital in emergency situations, and having a reliable device, in terms of functionality as well as performance, is critical. In situations with low-light conditions or other conditions experienced in emergencies, such as depressurization on an aircraft, it is paramount that the delivery system in question be fully functional, and that it indicates its functioning with ease and from a reasonable distance. Current flow indication devices are purely mechanical, and can get jammed or may break, or suffer any other failure seen in mechanical objects.

In certain applications, such as aircraft passenger oxygen supply systems, weight and space play are critical factors that impact the design and availability of such systems. All aspects of the oxygen delivery system are analyzed for efficiency and weight/space considerations, including a flow indicator on the oxygen system. Reliability and cost also factor into how a system can reliably supply oxygen flow indication without exhaustive testing of equipment and its operation. The present invention provides a simple and reliable method by which oxygen flow can be determined and indicated to a passenger or medical patient/personnel at the delivery end of the gas flow, e.g. the oxygen mask.

U.S. Pat. No. 7,730,847 to Redd et al, incorporated fully herein by reference, discloses a disposable breathing apparatus with a flow indicator that is located proximal to the mask for easy confirmation of the operational status of the system. Redd teaches the need for confirmation of the flow of oxygen at the mask as opposed to the source of the oxygen. U.S. Pat. No. 7,298,280 to Voege, et al., incorporated fully herein by reference, discloses a fluid flow indicator for monitoring and indicating fluid flow wherein the fluid pressure activates a pressure switch to indicate the presence of fluid movement in a tube or conduit. In a preferred embodiment, the pressure switch is observable from outside the conduit so that flow can be verified to a patient, passenger, or other fluid recipient.

SUMMARY OF THE INVENTION

The present invention is a flow indicator device and method that employs the movement of a fluid such as oxygen in a tube to power an illumination device used to indicate the presence of the flow itself. The indicator device utilizes one or a plurality of the techniques described herein to generate energy utilizing a flow present in tubing/piping that connect a manifold for dispensing breathing oxygen or air to a mask, cannula or other oral/oral-nasal device.

A first preferred method of power generation is the direct generation of a voltage and current by gas flow over carbon nanotubes and semiconductors. By employing Bernoulli's principle coupled with the Seebeck effect, a measurable voltage and current can be generated by utilizing a flow of a gas over a layer of doped silicon/germanium, applied to single/multiwall carbon nanotubes. Testing shows that the energy generated can be used in energy conversion devices and, more importantly, gas flow sensors. Using a clamp, multi-part system, or insert with an angle incident to the direction of flow, the moving gas induces a pressure differential (and consequently temperature differential) that in turn generates a voltage/current. The voltage may be generated even by a very slow flow, and this voltage is employed in the delivery system in conjunction with an illumination device (luminescent paint, LED's, OLED's, etc) that requires very little power, to generate a visual indication when there is flow passing through this system. The response time on a device employing this technology may be within a couple of seconds, if not almost without delay, and beneficially the invention is "an active" measuring device, i.e., power is only generated when there is a flow over the system. This leads to savings of power and weight of the overall system.

Alternatively, the system may be powered by a structurally integrated, light-emitting device-based sensors for detecting a gas phase and dissolved oxygen. Certain gases, such as oxygen, may be detected using a photo luminescent dye with indicating results via an OLED, and integrating it into one small device. The dyes have two major properties that make them attractive as a photo sensing and illuminating material—photoluminescence intensity and lifespan. A similar system can be inserted anywhere in the oxygen dispensing tube, thereby reducing the number of connections while maintaining the level of service provided.

Other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 5 is an enlarged, perspective view of a photoluminescence film and window arrangement to detect flow therein through.

DETAILED DESCRIPTION OF THE PREFERRED EMBODIMENTS

Figure 1A:
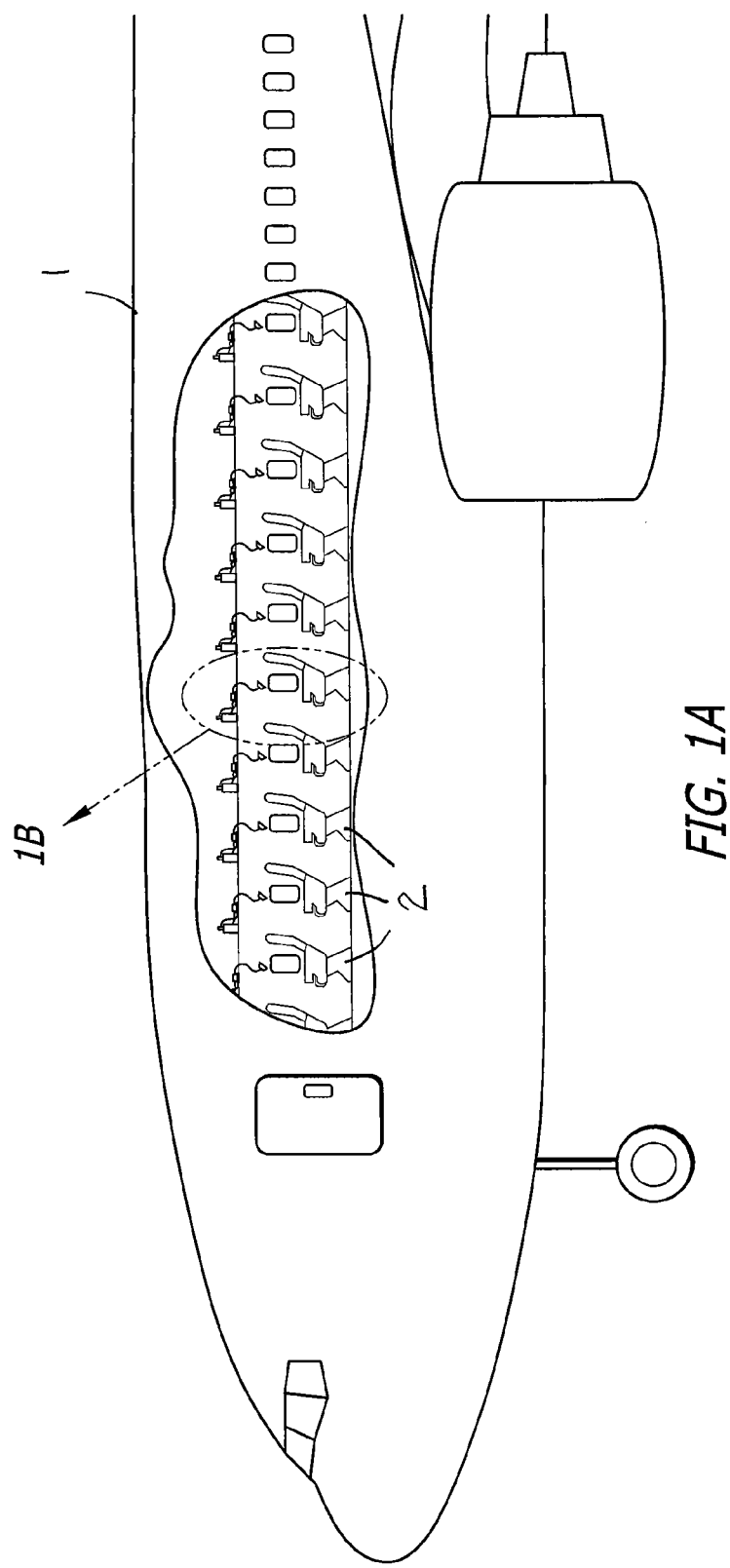
FIG. 1A shows a passenger oxygen supply system in the environment of an aircraft.

The present invention has multiple applications including medical, emergency, and other gas flow systems, but will be described for brevity in the context of an aircraft passenger oxygen delivery system. FIG. 1A illustrates and aircraft 1 having a row of seats 2, and above the seats 2 are oxygen delivery systems. The flow of a gas, such as oxygen, is detected in a system such as that shown in FIG. 1B according to one embodiment of the present invention. The flow indication device 30 is attached to two pieces of tubing/plumbing 20,40, with one end going downstream to the passenger through a breathing apparatus like a cannula, nasal/oral-nasal mask or other types of breathing apparatus 50. The other end going upstream with regards to the flow may connect to a manifold 10 that will eventually connect to the supply of breathable oxygen 8.

Figure 1B:
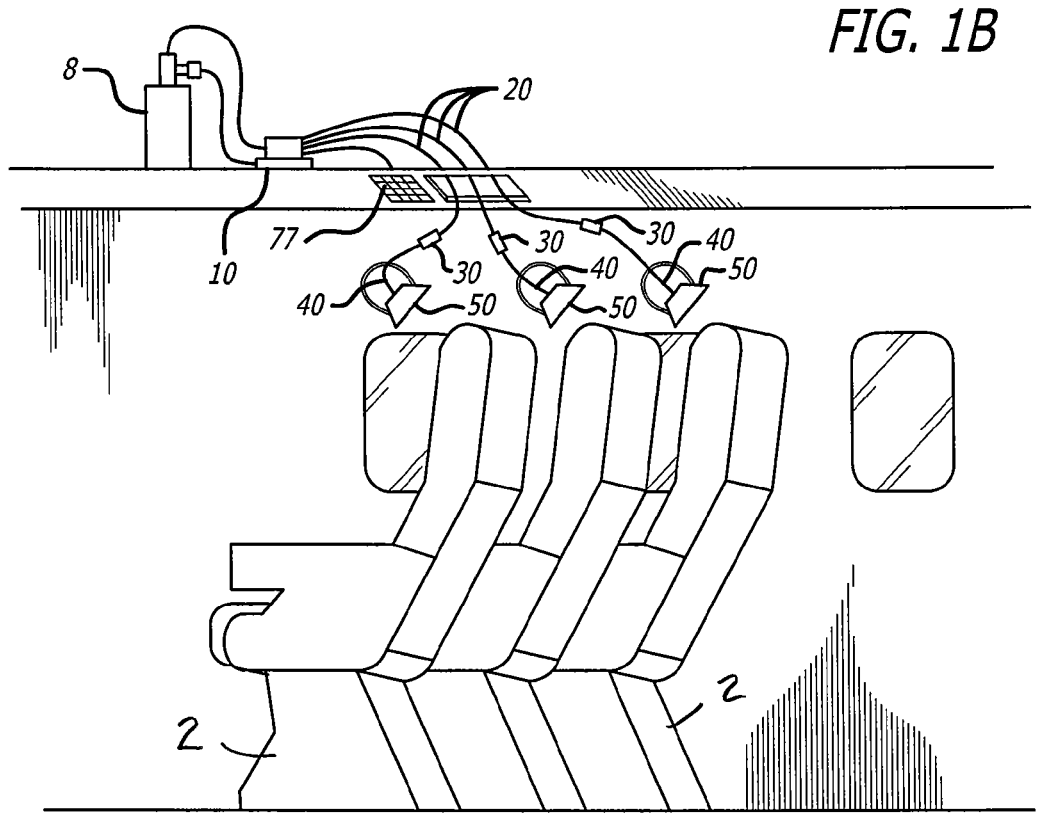
FIG. 1B an elevated perspective view of the oxygen supply system that can utilize the present invention.

The flow indicator 30 can be inserted between two pieces of tubing 20,40, as seen in FIG. 1B, but can also be miniaturized to where it can be inserted into the tubing 20 to minimize cost. It can be held in place by friction, or any number of devices that can fasten it to the tubing. Experimentation established that a direct generation of measurable voltages and currents are created when a gas such as oxygen is passed over a variety of solids even at a modest speed of a few meters per second. The underlying mechanism involves both Bernoulli's principle and the Seebeck effect. Pressure differences along streamlines give rise to temperature differences across the solid, and the temperature difference can be converted to a voltage differential. The electrical signal is quadratically dependent upon the Mach number M, and proportional to the Seebeck coefficient of the solid. The solid used in the present invention may be doped Si and Ge, single wall and multiwall carbon nanotubes, and graphite. Further research showed that this was true for gases including, but not limited to, oxygen, and that the effect was also present on multiwall nanotubes and doped semiconductors/metals over a large range of velocities. Testing confirmed flow velocities from 1 to 140 m/s, and demonstrated a quadratic relationship with the generated voltage.

Figure 2:
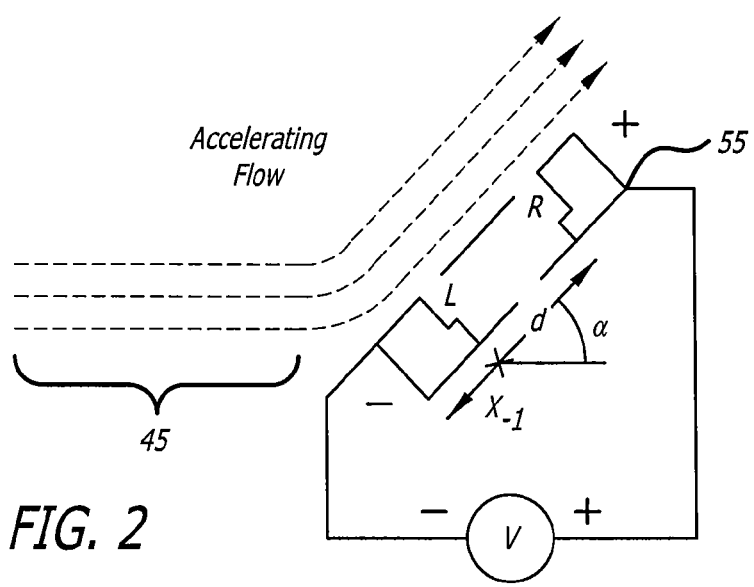
FIG. 2 is a schematic of a gas flow impinging on a substrate to create a photovoltaic change in the substrate.

FIG. 2 depicts a flow of a gas 45 over the selected substrate 55 where the optimum flow impingement angle, α=45° (with respect to the horizontal axis) is shown, producing the greatest differential in pressure (and consequently in temperature) between two terminals L, R, coated with silver emulsion to effectively yield the greatest amount of voltage V in the system. It was also discovered that at α=0° or 90°, no pressure gradient is formed, and no voltage is generated. This effect is described by Bernoulli's equation as follows:

$$\frac{P}{P_0} = \left[1 - \frac{1}{2}(\gamma - 1)M^2\right]^{\frac{\gamma}{\gamma-1}} \simeq 1 - \frac{\gamma}{2}M^2 \text{ (for } \gamma M^2 << 1). \quad (1)$$

The equation (1) above is valid for an adiabatic, steady inviscid flow of a gas, and provides a pressure difference that can be converted into a temperature difference using the ideal gas law in order to estimate the energy produced by the flow. For the case shown in FIG. 2, the temperature differential can be written as $$\frac{\Delta T}{T_0} \simeq \frac{1}{2}(\gamma - 1)(M_R^2 - M_L^2), \quad (2)$$

where the subscripts indicate the left L and right R terminals, as shown in FIG. 2. The temperature difference causing a voltage difference is called the Seebeck effect, and the relationship between voltage generated and the Seebeck effect is shown to be $$V = \frac{kT_0}{2}(\gamma - 1)S(M_R^2 - M_L^2) \propto \frac{kT_0}{2}(\gamma - 1)SM^2 \quad (3)$$

The generation of a theoretical voltage was tested with a variety of materials such as n-type Germanium (Ge) doped with Antimony (Sb), n and p-type Silicon (Si), and the carbon nanotubes discussed above, at various velocities to describe the relationship between Mach number M and voltage V, and correspondingly provided the Seebeck coefficient for the materials.

Figure 5:
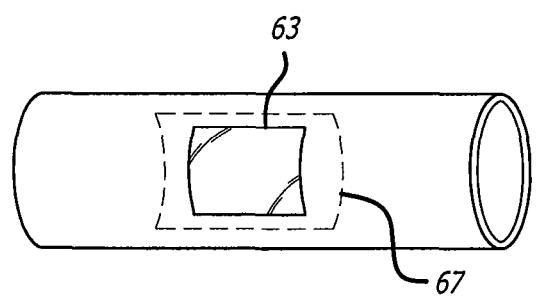

An alternate strategy to indicate flow utilizing the principle of photoluminescence can also be incorporated into the system. This alternative embodiment relies on the oxygen-sensitivity of materials like Pt- or Pd-octaethylporphyrin (PtOEP or PdOEP) embedded in polystyrene and tris (4,7-diphenyl-1,10-phenanthroline) RuII (Ru(dpp)) embedded in a sol-gel film. The reduction in components using this option leads to lower manufacturing and fabrication costs, while allowing for the production of a compact and efficient devices. The primary principle on which these sensors function is the dynamic quenching of the photoluminescence oxygen-sensing dyes in a film 67 (See FIG. 5). When oxygen collides with the dye, it causes a decrease in the photoluminescence intensity as well as the lifetime of the dye, which in some cases may be directly viewed through a window 63. By carefully monitoring these changes, the Stern-Volmer equation can be used, and is as follows:

$$\frac{I_0}{I} = \frac{\tau_0}{\tau} = 1 + K_{SV}[O_2] \quad (4)$$

where I is the photoluminescence intensity, τ is the photoluminescence lifetime, and $K_{SV}$ is the Stern-Volmer constant of the dye.

The aforementioned dye system is then structurally integrated with OLEDs that are of low-weight, low-voltage, flexible, and miniaturizable. OLEDs also lend themselves well to such applications due to the ease of manufacturability onto glass and plastic substrates in sizes in the order of micrometers to millimeters. The sensors in question can be fabricated in the order of millimeters where the OLED component is less than half a micrometer.

Figure 3:
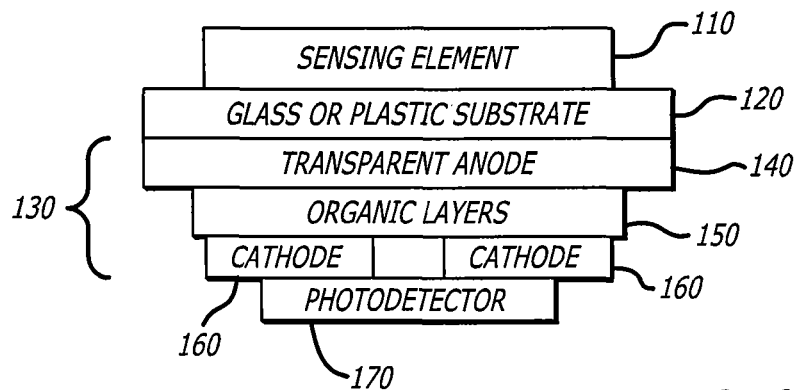
FIG. 3 is a diagram of an embodiment of an OLED based photoluminescence detecting system.

As shown in FIG. 3, a sensor may be comprised of the sensing element 110 embedded on a glass or plastic substrate 120, followed by the OLED component 130 that consists of the anode 140, organic layers 150, the cathode(s) 160, and finally, the photo detector layer 170. The nomenclature for "forward-detection" and "back-detection" comes from the position of the photo detector with respect to the OLED structure. Experimentation shows that even though the "forward-detection" as well as "backward-detection" systems work equally well for miniaturization, the silicon based photodiode and the photomultiplier tube technology are more suited to the geometry allowed by back-detector technology. This is due to the inherent fact that when the analyte sample is in front of the sensor system, this reduces the complexity in handling the samples and consequently reducing time and energy required for manufacturing.

The photo luminescent sensors, when integrated with the OLED system, can currently produce functional lifetimes of over 20,000 hours for certain emitters. As technology progresses, it is anticipated that this technology will produce sufficient lifetimes required of aerospace parts. Oxygen detection works on two different methodologies—monitoring photoluminescence intensity I, in DC mode and monitoring photoluminescence lifetime τ, in pulse mode. It is also noted that the response time for oxygen detection is much faster in the pulse system (<100 ns) as compared to the dc system (0.5-1000 μs), both of which provide sufficient resolution for oxygen detection in the aforementioned applications.

The flow indication apparatus of the present invention may utilize any photovoltaic material, e.g. a single/multiwall carbon nanotubes or doped silicon/germanium placed at an angle to where they can utilize the phenomenon of generating a pressure differential (which produces a temperature differential) and consequently uses the Seebeck effect to produce energy in the material to then illuminate a source. An oxygen-sensitive photo luminescent dye may also be utilized as a sensor, and is exposed to oxygen flow in order to provide power to an illuminated source, with the intention of displaying the presence of oxygen. Devices produced by SST sensing are incorporated into the design as an oxygen sensor, and are linked to an illuminated source to visually indicate the presence of flowing oxygen to the end user/flight crew.

The flow indication apparatus may also utilizes a chemical that is reactive to oxygen and can be used as a sensor to detect the presence and concentration of oxygen. Alternatively, the indicator may utilize chemical compounds that are reactive to oxygen, but do not create any new compounds or reaction byproducts that are harmful to the human body when inhaled. In a preferred embodiment, the indicator is a miniaturized device so that it fits inside the tubing connecting the oxygen source to the mask, supplying the required flow to power the device. It may also include an external sleeve that will act as a magnifying glass in order to help increase the range and conditions under which the device can be seen/witnessed. It may also have one or a plurality of colors emanating from the illuminated source. The illuminated source may be any combination of LED's, OLED's, or conductive/luminescent coating. The flow indication method can also be used to detect the concentration and saturation of oxygen present. This information can then be used to control the dispensing of oxygen to crew and passengers.

The thermo-voltaic power generation can be utilized in areas throughout an aircraft cabin (environmental control systems, air gaspers/ducts, pressurization equipment) to harvest (generate) and store power for the purposes of life support systems.

Figure 4A:
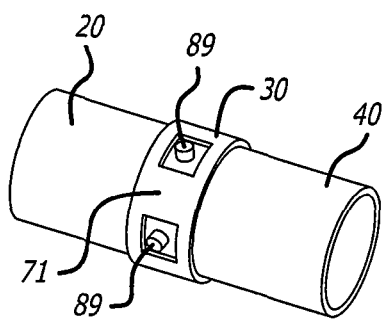
FIGS. 4A and B are an enlarged, elevated perspective view and cross-sectional views of an energy harvesting device incorporated into the present invention.
Figure 4B:
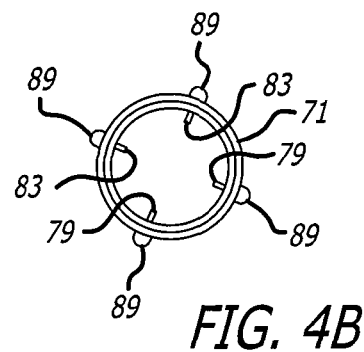

As shown in FIG. 4a, b, the present invention may also take the form of a breathing apparatus with a flow indicator 30 for indicating the flow of breathing-gas, where the flow indicator includes a housing 71 that defines a chamber 79 and is configured to connect to a breathing-gas supply; an energy harvesting device 83 located within the chamber; and a visual gas flow indicator 89 configured to be illuminated by power generated from the energy harvesting device when breathing-gas flows past the energy harvesting means. The visual gas flow indicator 89 may be selected from the group consisting of an LED, an LED bar graph, an LCD display, luminescent organic material, light emitting polymers, plastic scintillators, light-emitting MEMS, phosphorescent organic light emitting devices, incandescent bulbs, and lasers. Moreover, the energy harvesting device 83 may be a paddlewheel, a turbine, a screw, or a set of fan blades.

The invention may also come in the form of a flow indicator for indicating the flow of breathing-gas within a tube from an air source to a patient, wherein said flow indicator comprises: an indicator configured to provide a visual indication to a user when air is flowing within said tube from said air source to said patient, and an energy harvester configured to provide energy captured from air flowing within said tube to said indicator, wherein said energy is capable of powering said indicator to provide said visual indication to said user when air is flowing within said tube from said air source to said patient.

It will become apparent from the foregoing that while particular forms of the invention have been illustrated and described, various modifications can be made without departing from the spirit and scope of the invention. Accordingly, it is not intended that the invention be limited by the foregoing descriptions and illustrations.

We claim:

1. A flow indicator of a breathing apparatus that indicates a presence or flow of a breathable gas, comprising:
    a structure within a conduit for delivering the breathable gas, the structure undergoing a change as a result of a presence of the breathable gas or a movement of the breathable gas past the structure;
    a gas flow indicator that is actuated by the change in the structure to visually indicate the presence or flow of the breathable gas, wherein the gas flow indicator includes a photoluminescent dye configured to be quenched by oxygen of the breathable gas; and
    wherein the gas flow indicator is powered by the change in the structure without any outside power supply.

2. The flow indicator of claim 1, wherein the structure includes an energy harvesting device.

3. The flow indicator of claim 2, wherein the change in the structure is a temperature change that results in a voltage differential across the structure.

4. The flow indicator of claim 1 wherein the gas flow indicator includes a light emitting diode (LED).

5. The flow indicator of claim 1, further comprising a sleeve that fits over a tubing supplying the breathable gas, the sleeve configured to magnify a visual indication of the presence or flow of the breathable gas.

6. The flow indicator of claim 1, wherein the structure comprises a substrate, an anode, a cathode, and a photo detector layer.

7. The flow indicator of claim 6, wherein the structure uses back-detection.

8. The flow indicator of claim 1, further comprising a detector for detecting a concentration of oxygen present in the flow indicator.

9. A method for delivering oxygen to a user comprising:
    connecting the user to an oxygen supply via a conduit;
    incorporating into the conduit a gas flow indicator that indicates a flow of gas in the conduit, the gas flow indicator including a photoluminescent dye configured to be quenched by oxygen of the flow of gas;
    providing an indicator in conjunction with the gas flow indicator to display to the user a flow of oxygen in the conduit;
    wherein the gas flow indicator is powered solely by the oxygen in the conduit.

10. The method for delivering oxygen to a user of claim 9, wherein the gas flow indicator is powered by a movement of the oxygen in the conduit.

11. The method for delivering oxygen to a user of claim 9, wherein the gas flow indicator is powered by a reaction of the gas flow indicator to a presence of oxygen.

12. A passenger oxygen supply system, comprising:
    a flow indicator;
    a first tubing attached to an upstream side of the flow indicator, the first tubing configured to receive breathable oxygen from a manifold; and a second tubing attached to a downstream side of the flow indicator, the second tubing configured to provide the breathable oxygen to a passenger via a breathing apparatus;

wherein the flow indicator includes a structure configured to undergo a temperature change that results in a voltage differential across the structure as a result of a presence of the breathable oxygen or a movement of the breathable oxygen past the structure, and the flow indicator is configured to be actuated by the change in the structure to visually indicate the presence or movement of the breathable oxygen without any outside power supply, the flow indicator including a photoluminescent dye configured to be quenched by the breathable oxygen.

13. The passenger oxygen supply system of claim 12, wherein the structure comprises a surface doped with Silicon and Germanium.

14. The passenger oxygen supply system of claim 12, wherein the structure comprises carbon nanotubes.

\* \* \* \* \*